United States Patent [19]
Knutson et al.

[11] Patent Number: 5,622,941
[45] Date of Patent: Apr. 22, 1997

[54] ORAL 1 α-HYDROXYPREVITAMIN D

[75] Inventors: Joyce C. Knutson, Madison; Charles W. Bishop, Verona; Charles R. Valliere, Madison, all of Wis.

[73] Assignee: Lunar Corporation, Madison, Wis.

[21] Appl. No.: 188,942

[22] Filed: Jan. 26, 1994

Related U.S. Application Data

[63] Continuation of Ser. No. 901,886, Jun. 22, 1992, abandoned.

[51] Int. Cl.$^6$ .................................................. A61K 31/59
[52] U.S. Cl. ............................................................ 514/167
[58] Field of Search ............................................. 514/167

[56] References Cited

U.S. PATENT DOCUMENTS

| | | | |
|---|---|---|---|
| 2,216,719 | 10/1940 | Boer | 260/297 |
| 2,434,015 | 1/1948 | Rosenberg et al. | 167/81 |
| 4,230,701 | 10/1980 | Holick et al. | 514/167 |
| 4,335,120 | 6/1982 | Holick et al. | 514/167 |
| 4,505,906 | 3/1985 | DeLuca et al. | 514/167 |
| 4,539,153 | 9/1985 | Vandewalle et al. | 260/397.2 |
| 4,728,643 | 3/1988 | Holick et al. | 514/167 |
| 5,013,728 | 5/1991 | Grodberg | 514/171 |

FOREIGN PATENT DOCUMENTS

| | | |
|---|---|---|
| 0070588 | 1/1983 | European Pat. Off. . |
| 0215956 | 4/1987 | European Pat. Off. . |
| 59-010562 | 4/1984 | Japan . |
| WO84/04527 | 5/1984 | WIPO . |
| WO92/09271 | 6/1992 | WIPO . |

OTHER PUBLICATIONS

*Transactions of the Association of American Physicians*, vol. XCII, 1979, pp. 54–63, M. F. Holick, S. C. McNeill, J. A. MacLaughlin, S. A. Holick, M. B. Clark and J. T. Potts, Jr., "Physiologic Implications of the Formation of Previtamin D in Skin".

*Chemical Abstracts*, vol. 110, No. 10, 1989, Columbus, Ohio, Abstract No. 84136v, M. Takahashi, H. Mochizuki, "Enteric–Soluble Capsule Base Composed of Poly(Ethylene Glycol) or Its Substitutes and Cellulose Acetate Phthalate or Hydroxypropyl Methyl Cellulose Phthalate".

*Harrison's Principles of Internal Medicine*: Part Eleven, "Disorders of Bone & Mineral Metabolism," Chapter 335, E. Brauwald et al., (eds.) McGraw–Hill, New York (1987) pp. 1860–1865.

M. L. Curtin and W. H. Okamura, *J. Am. Chem. Soc.*, vol. 113 (1991) pp. 6958–6966.

*Primary Examiner*—Marianne M. Cintins
*Assistant Examiner*—Minna Moezie
*Attorney, Agent, or Firm*—Teresa J. Welch; Stroud, Stroud, Willink, Thompson & Howard

[57] ABSTRACT

Method of increasing activated vitamin D blood level by administering orally a 1α-hydroxyprevitamin D. This previtamin D form increases vitamin D blood level without significant risk of hypercalcemia associated with other oral dosing of vitamin D forms. The 1α-hydroxyprevitamin is compounded into a pharmaceutical composition in combination with a pharmaceutically acceptable excipient.

4 Claims, No Drawings

ORAL 1 α-HYDROXYPREVITAMIN D

This is a continuation of application Ser. No. 07/901,886 filed Jun. 22, 1992, now abandoned.

TECHNICAL FIELD

This invention relates to a method for increasing the blood level of active vitamin D compounds. More specifically, the invention relates to orally administering the 1α-hydroxylated previtamin form of vitamin D compounds in order to increase the blood level of the corresponding active vitamin D compound.

BACKGROUND OF THE INVENTION

Vitamin D is known to be important in the regulation of calcium metabolism in animals and man. See, *Harrison's Principals of Internal Medicine*: Part Eleven, "Disorders of Bone and Mineral Metabolism," Chapter 335, E. Braunwald et al., (eds.), McGraw-Hill, New York (1987) pp. 1860–1865.

Vitamin $D_3$ is synthesized endogenously in the skin of animals and man from 7-dehydrocholesterol by an ultraviolet-mediated photochemical reaction which breaks the B ring of the 7-dehydrocholesterol between carbon-4 and carbon-9 to form previtamin $D_3$. The triene previtamin $D_3$ is unstable and over time thermally converts to vitamin $D_3$. At normal body temperature an equilibrium exists between previtamin $D_3$ and vitamin $D_3$, as seen below. As vitamin $D_3$ is further metabolized in vivo this equilibrium shifts to the vitamin $D_3$ form.

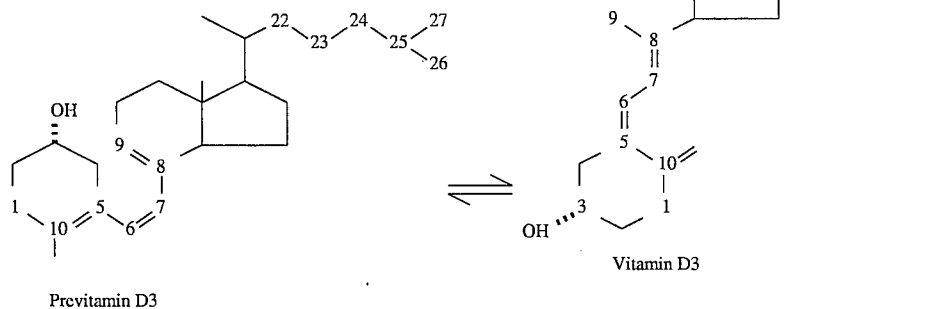

Previtamin D3 ⇌ Vitamin D3

It is known that vitamin $D_3$ must be hydroxylated in the carbon-1 and the carbon-25 position before it is activated, i.e., before it will produce a biological response. A similar metabolism appears to be required to activate the other forms of vitamin D, e.g., vitamin $D_2$ and vitamin $D_4$. As is generally understood and used herein, the term "vitamin D" is intended to include vitamins $D_3$, $D_2$, and $D_4$. The term "activated vitamin D," as used herein, is intended to refer to vitamin D which has been hydroxylated in at least the carbon-1 position of the A ring, e.g., 1α-hydroxyvitamin $D_3$.

Functionally, vitamin D is more appropriately considered a hormone than a vitamin. When activated, vitamin D interacts with a vitamin D receptor protein and this interaction ultimately results in some form of biological response. For example, 1α,25-dihydroxyvitamin $D_3$ is known to be a potent stimulator of calcium absorption from the intestine, such absorption is mediated by the interaction of the 1α,25-dihydroxyvitamin $D_3$ molecule and the vitamin D receptor protein located in the epithelial cells (enterocytes) which line the intestine.

In recent years it has become evident that the vitamin D receptor protein is widely distributed in the bodies of animals and man. Thus, it is not surprising that in addition to influencing calcium homeostasis, activated vitamin D has been implicated in osteogenesis, modulation of immune response, modulation of the process of insulin secretion by the pancreatic B cell, muscle cell function and the differentiation and growth of epidermal and hemopoietic tissues.

Such a wide range of biological actions suggests that the activated forms of vitamin D compounds should be valuable therapeutic agents for a wide range of maladies such as metabolic bone disease, osteoporosis, psoriasis, psoriatic arthritis, breast cancer and HIV infection. Unfortunately, when these agents are administered orally, the potent stimulation of calcium absorption by activated vitamin D can readily cause a dangerous hypercalcemia before the desired therapeutic response is obtained. For this reason, the activated vitamin D compounds are generally considered to have a low therapeutic to toxic ratio or low therapeutic index. Additionally, the presently known oral formulations when administered produce an unphysiologically rapid increase in the blood level of both calcium and activated vitamin D hormone followed by an almost as rapid decrease in the blood level of activated vitamin D hormone. Such rapid peaks and valleys of either the blood calcium or the activated vitamin D hormone are undesirable and perhaps harmful.

Recognizing the great potential of activated vitamin D as a therapeutic agent, alternative routes of administration which would allow higher sustained blood levels to be achieved and yet avoid the toxicity problems presented by the oral dosage form have been sought. To this end, an injectable form of 1α,25-dihydroxyvitamin $D_3$ has been developed by Abbott Laboratories and is marketed under the trade name Calcijex for the management of hypocalcemia in patients undergoing chronic renal dialysis. Topical and transdermal forms of the drug have also been suggested by Holick, U.S. Pat. No. 4,230,701.

These alternative routes of administration, however, lack the convenience and the reliability of an oral dosage form and, to that extent, have diminished the practicality and attractiveness of activated vitamin D compounds as therapeutic agents. What is needed, is an oral dosage form which produces a more physiological sustained increase in the blood level of activated vitamin D and has a more acceptable therapeutic index than is presently possible with heretofore known oral formulations of activated vitamin D.

SUMMARY OF THE INVENTION

The present invention responds specifically to the long-felt need heretofore unmet by the prior art and especially with a view to overcoming the inherent inadequacies of oral vitamin D formulations. The present invention provides a pharmaceutical composition and method for increasing activated vitamin D blood level by administering orally a compound of formula (I) as defined hereinbelow. The compounds of formula (I) include 1α-hydroxyprevitamin D and 1α,25-dihydroxyprevitamin D.

In accordance with the invention, it has been unexpectedly found that orally administered 1α,25-dihydroxyprevitamin D produces a sustained increase in the blood level of 1α,25-dihydroxyvitamin D and has a higher therapeutic index than does orally administered 1α,25-dihydroxyvitamin D. The increased activated vitamin D blood level is achieved with significantly less hypercalcemia than that resulting from oral dosing of the 1α,25-dihydroxyvitamin D.

The present invention is carried out by manufacturing 1α-hydroxyprevitamin D so that the 1α-hydroxyprevitamin D form remains relatively stable at room temperature. The 1α-hydroxyprevitamin D is then administered to an animal or human being in an oral dosage formulation. As the 1α-hydroxyprevitamin D is released from the oral dosage formulation, it is absorbed from the intestine into the blood. In the 1α-hydroxyprevitamin D form, the compound is inactive (i.e., does not bind to the vitamin D receptor protein) and does not stimulate intestinal calcium absorption. As the 1α-hydroxyprevitamin D is warmed by the core temperature of the animal or human being, it is thermally converted to the corresponding activated vitamin D, i.e., to its thermal isomer. The thermal conversion to the active form takes a sufficiently long period of time such that most of this conversion occurs in the time period after the 1α-hydroxyprevitamin D has been absorbed into the blood stream of the animal or human being. Thus, the 1α-hydroxyprevitamin D oral dosage formulation produces a greater sustained blood level of the corresponding activated vitamin D with significantly less stimulation of intestinal calcium absorption than is obtained by administering orally the corresponding activated vitamin D itself.

The foregoing and other advantages of the present invention are realized in one aspect thereof in a method for increasing the blood level of activated vitamin D in an animal or human being by administering orally an effective amount of 1α-hydroxyprevitamin D. A preferred embodiment of 1α-hydroxyprevitamin D is 1α,25-dihydroxyprevitamin $D_3$.

In another aspect, the invention is a method of increasing blood level of activated vitamin D for a sustained period of time, typically greater than four hours.

In yet another aspect, the invention is a method for treating osteoporosis by administering orally an effective amount of 1α-hydroxyprevitamin D. In a further aspect, the invention is a method of treating psoriasis by orally administering an effective amount of 1α-hydroxyprevitamin D.

The compounds of formula (I) are provided in pharmaceutical compositions in combination with a pharmaceutically acceptable excipient. These compositions constitute another aspect of the invention. Preferred compositions include compounds of formula (I) which include 1α,25-dihydroxyprevitamin $D_3$, 1α,25-dihydroxyprevitamin $D_2$, and 1α,25-dihydroxyprevitamin $D_4$.

Other advantages and a fuller appreciation of the specific adaptations, compositional variations and chemical and physical attributes of this invention will be gained upon examination of the detailed description and appended claims.

DETAILED DESCRIPTION OF THE INVENTION

The present invention relates broadly to therapeutic methods for ameliorating certain medical conditions by improving blood levels of activated vitamin D, and specifically, to improving such levels by administering an oral formulation with significantly less resultant hypercalcemia. These attributes are achieved through a novel treatment of a subject with the compounds of formula (I), as defined hereinbelow.

In accordance with the invention, it has been found that when substantially pure 1α-hydroxyprevitamin D is administered orally, it produces a greater sustained increase in the blood level of activated vitamin D and significantly less hypercalcemia and hypercalciuria than the same amount of activated vitamin D administered orally in previously known formulations. As used herein, the term "substantially pure" means at least 85% pure 1α-hydroxyprevitamin D. The term "sustained" as used herein means a blood level which remains relatively constant (i.e., ±10 pg./ml) for a period greater than a defined period.

The 1α-hydroxyprevitamin D of the present invention has the general formula (I):

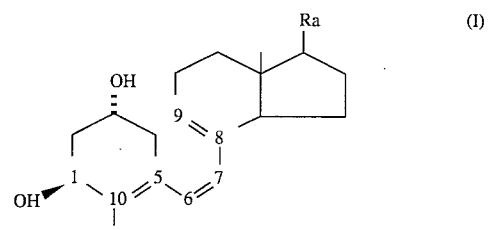

wherein $R_a$ is a side chain having at least 7 carbon atoms, and can be branched or unbranched, saturated or unsaturated, hetero-substituted or nonhetero-substituted, cyclic or noncyclic and wherein the thermal isomer (i.e., vitamin form) of the 1α-hydroxyprevitamin D of the general formula increases the serum calcium of the vitamin D deficient rat as determined by standard techniques used by biochemists in the vitamin D area. Among the preferred 1α-hydroxyprevitamin D of the present invention are those having the formula (II):

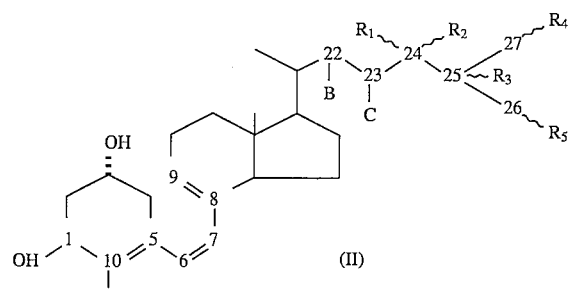

wherein B and C are either hydrogen or a carbon to carbon bond forming a double bond between C22 and C23; $R_1$, $R_3$, $R_4$ and $R_5$ are each independently hydrogen, hydroxy, lower alkyl, O-lower alkyl, O-lower acyl, O-aromatic acyl or flouro; and $R_2$ is hydrogen or lower alkyl. Most preferred among the compounds of formula (II), i.e., most preferred 1α-hydroxyprevitamin D compounds, are:

1α,25-dihydroxy-precholecalciferol [1α,25-$(OH)_2preD_3$];

1α,24,25-trihydroxy-precholecalciferol [1α,24,25-$(OH)_3preD_3$];

1α-hydroxy-precholecalciferol[1α-$(OH)preD_3$];

1α,24-dihydroxy-precholecalciferol[1α,24-$(OH)_2preD_3$];

1α,24-dihydroxy-25-fluoro-precholecalciferol[1α,24-$(OH)_225FpreD_3$];

1α,25-dihydroxy-preergocalciferol[1α,25-$(OH)_2preD_2$];

1α,24,25-trihydroxy-preergocalciferol[1α,24,25-$(OH)_3preD_2$];

1α-hydroxy-preergocalciferol[1α-$(OH)preD_2$];

1α,24-dihydroxy-preergocalciferol[1α,24-$(OH)_2preD_2$];

1α,24-dihydroxy-25-fluoro-preergocalciferol[1α,24-$(OH)_225FpreD_2$];

1α,25-dihydroxy-previtamin $D_4$[1α,25-$(OH)_2preD_4$];

1α,24,25-trihydroxy-previtamin $D_4$[1α,24,25-$(OH)_3preD_4$];

1α-hydroxy-previtamin $D_4$[1α-$(OH)preD_4$];

1α,24-dihydroxy-previtamin $D_4$[1α,24-$(OH)_2preD_4$]; and

1α,24-dihydroxy-25-fluoro-previtamin $D_4$1α,24-$(OH)_225FpreD_4$].

In the formulae shown in this specification and in the claims, a wavy line to substituent X indicates that the substituent can be stereoisomeric alternate forms. Wherever in this specification and in the claims the word "lower" is used as a modifier of alkyl or acyl, it is intended to identify a hydrocarbon chain having from about 1 to 4 carbon atoms which has either a straight chain or branched chain configuration. Specific examples of such hydrocarbon chains are: methyl, ethyl, propyl, butyl, isobutyl or t-butyl, and formyl, acetyl, propionyl, or butyryl. The term "aromatic acyl" as used herein and in the claims is meant to identify a benzoyl group or a substituted benzoyl group such as nitrobenzoyl or dinitrobenzoyl.

In a preferred embodiment, the compounds of formula (I) are provided in a crystalline form. 1α-Hydroxyprevitamin D in the crystalline form remains quite stable at room temperature with minimal conversion to the 1α-hydroxyvitamin D form. The compounds of formula (I), i.e., 1α-hydroxyprevitamin D, can be readily manufactured in crystalline form according to the procedure described in Vandewalle, U.S. Pat. No. 4,539,153.

The compounds of formula (I) are useful as active compounds in pharmaceutical compositions. Such compositions may include physiologically acceptable excipients or vehicles. These pharmaceutical compositions constitute another aspect of the invention.

The pharmacologically active compounds of this invention can be processed in accordance with conventional methods of pharmacy to produce medicinal agents for administration to patients, e.g., mammals, including human beings. For example, dosage forms of the compounds of formula (I) with conventional excipients, include admixtures suitable for oral administration. Dosage forms of the 1α-hydroxyprevitamin D can be combined with any nontoxic pharmaceutically acceptable carrier, such as cornstarch, lactose, or sucrose, which does not deleteriously react with the active compounds. The formulation can be produced in tablet, capsule, powders, troches and lozenges. Whatever method of formulation is used, care should be taken to avoid extended exposure to solvents and heat as under such conditions there will be a tendency for a portion 1α-hydroxyprevitamin D to convert to the 1α-hydroxyvitamin D form. Because heat and dissolution are preferably avoided, the preferred method of tablet formulation is the method known as dry granulation.

The dosage forms may also contain adjuvants, such as preserving or stabilizing adjuvants. They may also contain other therapeutically valuable substances or may contain more than one of the compounds specified herein and in the claims in admixture.

Advantageously, the compounds of the present invention or combinations thereof with other therapeutic agents can be administered in dosage amounts of from 0.1 to 100 micrograms per day. In relation to osteoporosis, doses from about 0.5 to about 25 micrograms per day are generally effective. If the compounds of the present invention are administered in combination with other therapeutic agents, the proportions of each of the compounds in the combination being administered will be dependent on the particular disease state being addressed. For example, in the case of osteoporosis, one may choose to administer the previtamin form of an activated vitamin D compound with an estrogen compound, Calcitriol, Calcitonin or a bisphosphonate. In practice, higher doses of the compounds of the present invention are used where therapeutic treatment of a disease state is the desired end, while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

The 1α-hydroxyprevitamin D is administered to the animal or human in oral dosage formulation. As the 1α-hydroxyprevitamin D is released from the oral dosage formulation, it is absorbed from the intestine into the blood. 1α-Hydroxyprevitamin D does nt interact with the vitamin D receptor protein of the enterocytes and, therefore, does not stimulate intestinal calcium absorption.

It is also known that the binding of activated vitamin D with the vitamin D protein receptor of the enterocyte induces the release of enzymes which degrade a significant portion df the unbound activated vitamin D present in the intestine. Such degradation decreases the amount of activated vitaminD available for absorption into the blood stream. Since 1α-hydroxyprevitamin D does not bind with the vitamin D receptor protein there is no enzyme induction. Thus, less degradation occurs in the intestine and a greater amount is available for absorption into the blood stream than is the case with the corresponding activated vitamin D.

As the 1α-hydroxyprevitamin D is warmed by the core temperature of the animal or human being, it is thermally converted to the corresponding activated vitamin D. The reaction time for thermal conversion to the active form is sufficiently long so that most of the conversion occurs over time after the 1α-hydroxyprevitamin D has been absorbed into the blood stream. Thus, the 1α-hydroxyprevitamin D oral dosage formulation produces a greater sustained blood level of the corresponding activated vitamin D with significantly less stimulation of intestinal calcium absorption than is possible with a comparable oral dosage amount of the activated vitamin D itself.

The present invention is further explained by the following examples which should not be construed by way of limiting the scope of the present invention. In the following examples, high pressure liquid chromatography (HPLC) was performed on a Waters Instrument, using a Zorbox SilODS column.

EXAMPLE 1

Time Course of 1α-hydroxyprevitamin D Conversion to 1α-hydroxyvitamin D

One and a half micrograms of 1α-hydroxyvitamin $D_2$ was dissolved in 2.00 ml ethanol. This solution was then subjected to a 60° C. water bath for 24 hours. Fractions of 1α-hydroxyprevitamin $D_2$[1α-OH-pre-$D_2$] were collected in nearly pure amounts from this treated sample. These previtamin fractions were pooled in a single test tube, dried under nitrogen gas on ice and eventually redissolved in 1.00 ml ethanol. The pooled fraction of previtamin, upon HPLC analysis, indicated 96% was previtamin at t=0 time.

A tube with the pooled previtamin was then placed in a 37° C. water bath. 50 μl aliquots were removed and placed into LVI tubes with a cold water jacket around them. Samples were chromatographed to determine the percent of 1α-hydroxyprevitamin $D_2$ and 1α-OH-$D_2$ present in each sample. Sampling times were 0, 0.5, 1.0, 1.5, 2.0, 2.5, 3.0, 3.5, 4.0, 6.0, and 8.0 hours. Results are presented below in Tables 1 and 2:

TABLE 1

1α-OH-$D_2$ SAMPLE PREPARATION

| SAMPLE | % PREVITAMIN | % 1α-OH-$D_2$ |
| --- | --- | --- |
| Starting Material | 0.00 | 99 |
| 24 hours at 60° C. | 8 | 92 |
| Pooled Fractions | 96 | 4 |

TABLE 2

TIME COURSE OF 1α-OH PREVITAMIN $D_2$

| SAMPLE (T = hrs) | % 1α-OH-PRE-$D_2$ | % 1α-OH-$D_2$ |
| --- | --- | --- |
| T = 0.0 | 96 | 4 |
| T = 0.5 | 93 | 7 |
| T = 1.0 | 90 | 10 |
| T = 1.5 | 86 | 13 |
| T = 2.0 | 83 | 17 |
| T = 2.5 | 79 | 21 |
| T = 3.0 | 77 | 23 |
| T = 3.5 | 73 | 27 |
| T = 4.0 | 71 | 29 |
| T = 6.0 | 61 | 39 |
| T = 8.0 | 52 | 48 |

These results indicate that at normal body temperature, a 50% conversion of 1α-hydroxyprevitamin $D_2$ to 1α-hydroxyvitamin $D_2$ in vitro required approximately eight hours. In vivo one would expect a similar rate of conversion. These data indicate that thermal conversion at normal body temperature is sufficiently slow that most of the 1α-hydroxyprevitamin D compound is absorbed into the blood stream in the previtamin form and conversion to the activated vitamin D counterpart occurs principally after absorption from the intestine. This results in a greater sustained blood level of activated vitamin D with less stimulation of intestinal calcium absorption than is seen with administering the corresponding activated vitamin D compound orally.

EXAMPLE 2

In Vitro Biological Activity 1,25-Dihydroxyprevitamin $D_3$ or 1,25-dihydroxyvitamin $D_3$ are incubated with the vitamin D receptor protein and tracer amounts of $^3$H-1,25-(OH)$_2D_2$ under standard conditions for a competitive binding assay. The amount of 1,25-dihydroxyprevitamin $D_3$ and 1,25-dihydroxyvitamin $D_3$ competitor is varied between 1.25 pg. and 1.25 ng. Concurrent with the incubations for binding a tube of 1,25-dihydroxyprevitamin $D_3$ is incubated at the same temperature and for the same length of time and is analyzed by HPLC for the amount of 1,25-dihydroxyprevitamin $D_3$ that has equilibrated to the vitamin form. The level of binding of the 1,25-dihydroxyprevitamin $D_3$ form is then corrected for the amount of the vitamin form that has been generated during the assay procedure.

These procedures show that the 1,25-dihydroxyprevitamin $D_3$ form has an affinity for the receptor less than 0.1 the affinity of the 1,25-dihyddroxyvitamin $D_3$ form.

EXAMPLE 3

Acute Hypercalcemia Testing

Male weanling rats are fed a vitamin D deficient diet containing normal Ca (0.47%) and P (0.3%). After approximately 4–6 weeks on this diet, the rats are separated into five groups and orally administered either 1,25-dihydroxyvitamin $D_3$ (0.06 or 0.12 ug/kg/day) or 1,25-dihydroxyprevitamin $D_3$ (0.06 or 0.12 ug/kg/day) in a vehicle such as lactose, or the vehicle alone (control), for 3 days. All animals are exsanguinated 24 hours after the last dose and the blood is analyzed for serum calcium and serum phosphorus. The results demonstrate that dosing with 1,25-dihydroxyvitamin $D_3$ causes a greater rise in serum calcium and serum phosphorus than comparable dosing with 1,25-dihydroxyprevitamin $D_3$.

EXAMPLE 4

Bioavailability Testing

Male weanling rats are fed a diet deficient in vitamin D and with normal calcium (0.47%). After a period of four weeks has elapsed, the rats are divided into two groups, and orally administered either 1α,25-dihydroxyprevitamin $D_3$ (0.25 μg/kg) in a vehicle such as lactose or the vehicle (control) alone. Four hours after administration, the rats are killed and their blood level of 1α,25-dihydroxyvitamin $D_3$ is measured using a standard technique.

Following this procedure demonstrates that the blood level of 1α,25-dihydroxyvitamin $D_3$ in rats that are administered 1α,25-dihydroxyprevitamin $D_3$ is significantly elevated over the blood level of control animals.

EXAMPLE 5

In Vivo Biological Activity Testing

Male weanling rats are fed a vitamin D deficient diet containing normal Ca (0.47%) and P (0.3%). After four weeks on this diet, the rats are separated into two groups and orally administered 0.42 μg/kg 1,25-dihyddroxyprevitamin $D_3$ in a vehicle such as lactose or the vehicle alone (control) for each of 14 days. Eight hours after the last dose, the rats are killed and the blood calcium, blood phosphorus, and blood 1,25-dihyddroxyvitamin $D_3$ levels are measured.

This procedure demonstrates that the serum calcium, serum phosphorus and serum 1,25-dihydroxyvitamin $D_3$ levels are higher in the 1,25-dihydroxyprevitamin $D_3$ dosed animals than in the control animals.

EXAMPLE 6

Pharmacokinetics Testing

Male weanling rats are fed a vitamin D deficient diet containing normal Ca (0.47%) and P (0.3%). After four weeks on this diet, the rats are separated into seventeen groups and orally administered either 1,25-dihyddroxyvitamin $D_3$ or 1,25-dihydroxyprevitamin $D_3$ in a vehicle such as lactose or the vehicle alone (control). One group is killed 8 hours after dosing with the vehicle. Eight groups are orally administered a single dose of either 1,25-dihydroxyprevitamin $D_3$ or 1,25-dihyddroxyvitamin $D_3$ and killed at 2, 4, 6, 9, 12, 18, 24, and 48 hours after dosing. The blood is collected and analyzed for 1,25-dihydroxyvitamin $D_3$ levels.

These procedures demonstrate that dosing with 1,25-dihyddroxyprevitamin $D_3$ results in 1,25-dihydroxyvitamin $D_3$ serum levels with a slower rise and longer duration than the 1,25-dihydroxyvitamin $D_3$ pharmacokinetics observed after dosing with 1,25-dihydroxyvitamin $D_3$.

EXAMPLE 7

Treatment of Osteoporosis

A clinical study is conducted with postmenopausal osteoporotic outpatients having ages between 55 and 75 years. The study involves up to 120 patients randomly divided into three treatment groups, and continues for 24 months. Two of the treatment groups receive constant dosages of orally administered $1\alpha,25$-dihydroxyprevitamin $D_3$ (u.i.d.; two different dose levels above 0.5 µg/day) and the other group receives a matching placebo. All patients maintain a normal intake of dietary calcium (500 to 800 mg/day) and refrain from using calcium supplements. Efficacy is evaluated by pretreatment and posttreatment comparisons of the patient groups with regard to (a) total body, radial, femoral, and/or spinal bone mineral density as determined by x-ray absorptiometry (DEXA), (b) bone biopsies of the iliac crest, and (c) determinations of serum osteocalcin. Safety is evaluated by comparisons of urinary hydroxyproline excretion, serum and urine calcium levels, creatinine clearance, blood urea nitrogen, and other routine determinations.

This study demonstrates that patients treated with orally administered $1\alpha,25$-dihydroxyprevitamin $D_3$ exhibit significantly higher total body, radial, femoral, and/or spinal bone densities relative to patients treated with placebo. The treated patients also exhibit significant elevations in serum osteocalcin. Bone biopsies from the treated patients show that $1\alpha,25$-dihydroxyprevitamin $D_3$ stimulates normal bone formation. The monitored safety parameters confirm an insignificant incidence of hypercalcemia or hypercalciuria, or any other metabolic disturbance with $1\alpha,25$-dihydroxyprevitamin $D_3$.

EXAMPLE 8

Prevention of Osteoporosis

A clinical study is conducted with healthy postmenopausal women having ages between 55 and 60 years. The study involves up to 80 patients randomly divided into two treatment groups, and continues for 12 to 24 months. One treatment group receives a constant dosage of $1\alpha,25$-dihydroxyprevitamin $D_3$ (u.i.d.; a dose level above 0.5 µg/day) and the other receives a matching placebo. The study is conducted as indicated in Example 6 above.

This study demonstrates that patients treated with $1\alpha,25$-dihydroxyprevitamin $D_3$ exhibit reduced losses in total body, radial, femoral, and/or spinal bone densities relative to baseline values. In contrast, patients treated with placebo show significant losses in these parameters relative to baseline values. The monitored safety parameters confirm the safety of long-term le, $1\alpha,25$-dihyddroxyprevitamin $D_3$ administration at this dose level.

EXAMPLE 9

Prevention of Hypocalcemia and Bone Loss in Renal Dialysis Patients

A 12-month double-blind placebo-controlled clinical trial is conducted with 30 men and/or women with renal disease who are undergoing chronic hemodialysis. All patients enter an 8-week control period during which time they receive a maintenance dose of vitamin $D_3$ (400 IU/day). After this control period, the patients are randomized into two treatment groups: one group receives a constant dosage of $1\alpha,25$-dihydroxyprevitamin $D_4$ (u.i.d., a dosage greater than 3.0 µg/day), and the other group receives a matching placebo. Both treatment groups receive a maintenance dosage of vitamin $D_3$, maintain a normal intake of dietary calcium, and refrain from using calcium supplements. Efficacy is evaluated by pretreatment and posttreatment comparisons of the two patient groups with regard to (a) direct measurements of intestinal calcium absorption, (b) total body, radial, femoral, and/or spinal bone mineral density, and (c) determinations of serum calcium and osteocalcin. Safety is evaluated by regular monitoring of serum calcium.

Analysis of the clinical data shows that $1\alpha,25$-dihydroxyprevitamin $D_4$ significantly increases serum osteocalcin levels and intestinal calcium absorption, as determined by measurements using a single- or double- isotope technique. Patients treated with this compound show normalized serum calcium levels, stable values for total body, radial, femoral, and/or spinal bone densities relative to baseline values. In contrast, patients treated with placebo show frequent hypocalcemia, significant reductions in total body, radial, femoral, and/or spinal bone density. An insignificant incidence of hypercalcemia is observed in the treated group.

EXAMPLE 10

Treatment of Psoriasis

An oral dosage formulation containing $1\alpha,24$-dihyddroxyprevitamin $D_2$ is evaluated in a double blind study for therapeutic efficacy of the formulation in the treatment of dermatitis (contact and ectopic). The formulation evaluated contains 1.0 to 2.0 µg of $1\alpha,24$-dihyddroxyprevitamin $D_2$. The control formulation is identical except that it does not contain the $1\alpha,24$-dihyddroxyprevitamin $D_2$. The patients are treated in an outpatient clinic and are divided into an experimental and control population. They are instructed to take the medication once a day, in the morning before breakfast.

In each patient (experimental and control) an area of the skin containing a lesion is selected which is ordinarily covered by clothing and the patients are instructed not to expose the skin area selected for study to sunlight. The area of the lesion is estimated and recorded, and the lesion(s) is photographed. Relevant details of the photographic procedure are recorded so as to be reproduced when the lesions are next photographed (distance, aperture, angle, background, etc.).

Evaluations of erythema, scaling, and thickness are conducted at weekly intervals by a physician. The final evaluation is usually carried out at the end of four to six weeks of treatment. The results of the study show that daily oral administration of 1,24-dihyddroxyprevitamin $D_2$ significantly reduces the degree of erythema, scaling, and thickness versus the control patients.

In summary, the present invention provides methods for ameliorating certain medical conditions by improving blood levels of activated vitamin D. The improved levels are achieved by administration of an oral formulation of 1α-hydroxyprevitamin D. The 1α-hydroxyprevitamin D is not active in the intestine to stimulate calcium absorption, thus, reducing significantly the risk of hypercalcemia associated with known oral formulation of vitamin D. Conversion of the previtamin form to the activated vitamin D occurs over time, primarily in the blood after absorption of the previtamin from the intestine, thus, producing higher levels for a greater sustained time per administration.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method for increasing the blood level of activated vitamin D in an animal or human comprirsing the step of administering orally to the animal or human an effective amount of substantially pure, crystalline 1α-hydroxprevitamin D along with one or more pharmaceutically acceptable excipients, wherein said 1α-hydroxprevitamin D is 1α,25-hydroxprevitamin $D_3$.

2. The method of claim 1, further comprising the step of sustaining the blood level of activated vitamin D for a period of time greater than four hours [wherein said 1α-hydroxprevitamin D is 1α,25-hydroxprevitamin $D_3$].

3. The method of claim 1, further comprising formulating said 1α-hydroxprevitamin D in a solvent-free formulation.

4. The method of claim 1, wherein said amount of 1α-hydroxyprevitamin D is in a unit dosage form sufficient to deliver about 0.1 µg/day to about 100 µg/day.

* * * * *

UNITED STATES PATENT AND TRADEMARK OFFICE
CERTIFICATE OF CORRECTION

PATENT NO. : 5,622,941
DATED : April 22, 1997
INVENTOR(S) : Knutson et al.

It is certified that error appears in the above-indentified patent and that said Letters Patent is hereby corrected as shown below:

Column 12, line 9, "comprirsing" should read --comprising--.

Column 12, lines 11-12 and 13, "1α-hydroxprevitamin D" should read --1α-hydroxyprevitamin D--.

Column 12, lines 13-14, "1α,25-hydroxprevitamin $D_3$" should read --1α,25-dihydroxyprevitamin $D_3$--.

Column 12, lines 19-20, delete [wherein said 1α-hydroxprevitamin D is 1α,25-hydroxprevitamin $D_3$].

Column 12, line 23, "1α-hydroxprevitamin D" should read --1α-hydroxyprevitamin D--.

Signed and Sealed this

Seventh Day of October, 1997

Attest:

BRUCE LEHMAN

*Attesting Officer*  *Commissioner of Patents and Trademarks*